United States Patent
Rugfelt et al.

(10) Patent No.: US 6,918,393 B2
(45) Date of Patent: Jul. 19, 2005

(54) CONFIGURATION FOR SUPPORTING AND STABILIZING AN INJURED PERSON

(75) Inventors: Hakan Rugfelt, Falsterbo (SE); Bo Renberg, Degerfors (SE)

(73) Assignee: Kohlbrat & Bunz Gesellschaft mbH, Radstadt (AU)

( * ) Notice: Subject to any disclaimer, the term of this patent is extended or adjusted under 35 U.S.C. 154(b) by 192 days.

(21) Appl. No.: 10/132,762

(22) Filed: Apr. 25, 2002

(65) Prior Publication Data

US 2003/0139694 A1 Jul. 24, 2003

(Under 37 CFR 1.47)

Related U.S. Application Data

(63) Continuation of application No. PCT/AT00/00276, filed on Oct. 24, 2000.

(30) Foreign Application Priority Data

Oct. 25, 1999 (AT) .............................................. 1796/99

(51) Int. Cl.$^7$ .............................................. A61G 15/00
(52) U.S. Cl. ....................... 128/845; 128/846; 128/869; 128/870; 5/630
(58) Field of Search ................................ 128/845, 846, 128/869, 870, 876; 5/454, 621, 626, 630, 633, 634, 694, 708, 713

(56) References Cited

U.S. PATENT DOCUMENTS

| | | | |
|---|---|---|---|
| 3,745,998 A | | 7/1973 | Rose |
| 3,762,404 A | * | 10/1973 | Sakita ........................... 602/6 |
| 4,261,349 A | | 4/1981 | Lambson et al. |
| 4,885,811 A | * | 12/1989 | Hayes ....................... 5/81.1 T |
| 5,154,185 A | | 10/1992 | Latimer et al. |
| 5,718,669 A | | 2/1998 | Marble |
| 5,906,205 A | * | 5/1999 | Hiebert ....................... 128/845 |
| 6,276,365 B1 | * | 8/2001 | Stelzenmuller ............. 128/869 |
| 6,318,372 B1 | * | 11/2001 | Hiebert ....................... 128/869 |

FOREIGN PATENT DOCUMENTS

| | | |
|---|---|---|
| CH | 661 204 A5 | 7/1987 |
| FR | 2 530 946 | 2/1984 |
| FR | 2 638 965 | 5/1990 |
| WO | WO 99/16392 | 4/1999 |
| WO | WO 99/47085 | 9/1999 |

* cited by examiner

*Primary Examiner*—Michael A. Brown
(74) *Attorney, Agent, or Firm*—Laurence A. Greenberg; Werner H. Stemer; Ralph E. Locher (57) ABSTRACT

The invention relates to a device for supporting and stabilizing an injured person. The device comprises a flexible film element whose two films define an air-tight inner space in between them that can be evacuated and in which loose particle-containing chambers are provided. The inventive device comprises a torso part and a head part that is provided on both sides with shoulder rests.

25 Claims, 6 Drawing Sheets

CONFIGURATION FOR SUPPORTING AND STABILIZING AN INJURED PERSON

CROSS-REFERENCE TO RELATED APPLICATION

This application is a continuation of copending International Application No. PCT/AT00/00276, filed Oct. 24, 2000, which designated the United States and which was not published in English.

BACKGROUND OF THE INVENTION

Field of the Invention

The invention relates to a configuration for supporting and stabilizing an injured person or injured body part, with a flexible film element which can be secured round the body part and whose two films enclose an airtight evacuable inner space wherein chambers are provided which contain loose particles.

Rescue and transportation configurations of this kind, also referred to as vacuum mattresses, vacuum jackets and vacuum splints, have a casing made of an airtight plastic film and a filling consisting of plastic granules, in particular foamed polystyrene beads, and, after they have been fitted and fixed to a body part that is to be immobilized, they can be evacuated by means of a suction pump. This leads to a tight packing of the granule filling, and thus to a stiffening of the flexible element, which in this way forms a substantially stiff casing or sleeve round the body part. To permit fixing to the body part in a manner which is as versatile as possible, the fastening straps are arranged in the circumferential direction of the body part and are provided with conventional adjustable attachments. Vacuum mattresses and vacuum splints are intended principally for a horizontal position of use. When used in a non-horizontal position, for example when the injured persons are seated, there is a risk that the filling in a higher area will form a thinner layer or even be absent because it has moved from the top downward during handling. It has therefore been proposed (U.S. Pat. No. 5,154,185) to divide the inner space into narrower chambers by means of horizontal dividing walls, said dividing walls having apertures which are just large enough to allow some of the filling to be forced through by hand. The horizontal dividing walls are secured directly to the film facing the patient, and on the outside to an inner layer which is in turn connected to the outer film. The two films of airtight material are connected to one another along their edges. The production of such an arrangement is therefore relatively difficult since the dividing walls have to be secured from the inside of the chambers at least on one side.

The support element in U.S. Pat. No. 5,154,185 can also be fixed to a seat, wherein case longitudinal webs which provide stiffening are used in the upper body area. A special head and neck support is not provided.

International PCT application WO 99/16392 A discloses another such assembly which is likewise intended in particular for upright transportation of an injured person, having an evacuable support cushion for the upper body and a separate evacuable support cushion for the head which are secured on a stiffening frame. The cushions consist of two airtight films which are connected to one another along their edges and at some points in the inside. The inner connections prevent free movement of the granules, so that a fairly uniform distribution is largely maintained despite the use in the upright position. The production of this support arrangement too is relatively complicated.

SUMMARY OF THE INVENTION

The invention therefore has the object of making available an arrangement of the abovementioned type which is easier to produce and provides improved head and neck stabilization, and the invention achieves this object by virtue of the fact that the head part is provided on both sides with a shoulder support. In the flat state of the film element, the shoulder support is formed by flaps which protrude laterally above the trunk part and which are bent forward about the head so that they rest on the shoulders. The flaps are in particular of such a size that they can be bent downward and cover the area of the collarbones. Connecting straps extending obliquely downward to the front of the trunk part are preferably provided. After evacuation, the flaps lying on the shoulders provide for stable securing of the head part on the shoulder of the injured person immobilized by the trunk part, i.e. an excellent head support is achieved without stiffening frame parts or insert parts.

Inherent stiffness in the vertical direction, advantageous for stabilizing a seated injured person, can be achieved in particular by arranging a further film piece on the outside of the film directed away from the injured person, which further film piece is fastened to the film by means of mutually intersecting connecting seams.

The configuration for supporting and stabilizing an injured body part is conventionally provided with fastening straps which can be closed in the circumferential direction of the body part. In order to prevent the particle filling from slipping downward under the effect of gravity when used on a seated patient, it is further preferably provided that the chambers extend parallel to the fastening straps. The chambers preferably partially superpose one another so that, with the inner space evacuated, particles from adjacent chambers complement one another to give a substantially uniform layer. The particularly simple production of the film element can be achieved in particular by the fact that the inner space is divided into at least three compartments by at least two air-permeable flexible dividing walls, and the chambers are formed in at least one of the three compartments.

Dividing the inner space parallel to the films into three compartments, in other words flat subsidiary areas, makes it possible to produce the arrangement in subsidiary layers so that the connection of the individual elements can be provided and executed at readily accessible points. Building on these basic features, various preferred embodiments can be obtained.

Thus, a first embodiment has only three compartments, the chambers being provided in the middle compartment and being formed by webs between the flexible dividing walls. The webs are arranged obliquely so that the chambers and the particles contained therein overlap.

In a second embodiment of an inner element of this kind, the oblique webs are formed by an undulating insert connected to the two flexible dividing walls at each area of return.

The two dividing walls enclosing the chambers thus each represent a separately produced inner element which is filled with the particles and is secured along its periphery in the edge area of a film. The second film is then connected to the first one. However, the prefabricated inner element forming an insert body can also be inserted between the edges of the two films and can be joined together with these. The insert body can be produced for example from a plurality of strips stitched together in an approximate Z shape. The two outer compartments are empty, so that the dividing walls bear on the films from the inside when the air is evacuated.

In a further embodiment, the inner space is likewise divided into three compartments, but with the chambers being provided in the two outer compartments and the middle compartment being empty. In this embodiment, a dividing wall and a film each are divided into chambers by a plurality of parallel connecting seams, the chambers are filled with particles, and the two films are then connected along their edges.

Connecting seams opposite one another are each offset by half the width of the chamber so that the two rows of chambers overlap one another. The overlap of the chambers results in an approximately uniform distribution of the filling despite the absence of particles in the area of the connecting seams.

In a third embodiment, the inner space is divided into five compartments by four dividing walls, and the chambers are provided in the second and fourth compartments. For this purpose, the dividing walls are connected to one another in pairs by means of parallel connecting seams, and in this embodiment too the connecting seams opposite one another are offset by in each case half the width of the chamber so that in each case one connecting seam lies in the area of a chamber apex and the two rows of chambers again overlap one another. In the production of this embodiment, the two insert bodies consisting in each case of two dividing walls are first produced and filled with particles. The insert bodies are then secured along their periphery in the edge area of a film, and the two films are finally connected along their edges.

Since the films are preferably woven from a polyurethane and the dividing walls and webs are preferably woven from lengths of fabric made of polypropylene fibers, the films are preferably welded to one another and to the dividing walls, and the dividing walls are sewn to one another and to the webs. The width of the chambers in the head part is preferably smaller than in the trunk part.

Preferred embodiments of the arrangement form a jacket, for stabilizing the upper body, and a neck support.

Other features which are considered as characteristic for the invention are set forth in the appended claims.

Although the invention is illustrated and described herein as embodied in configuration for supporting and stabilizing an injured person, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
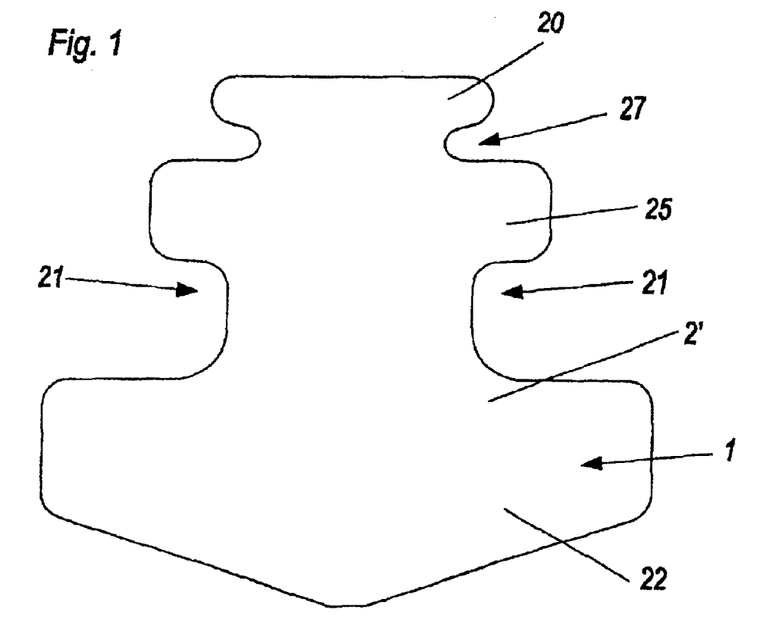
FIG. 1 is a plan view of an arrangement for stabilizing the upper body and head, showing the side which bears on the patient.

A configuration for stabilizing and supporting the upper body of an injured person has a film element 1 with a head part 20 and with a trunk part 22 separated by arm cutouts 21.

Figure 2:
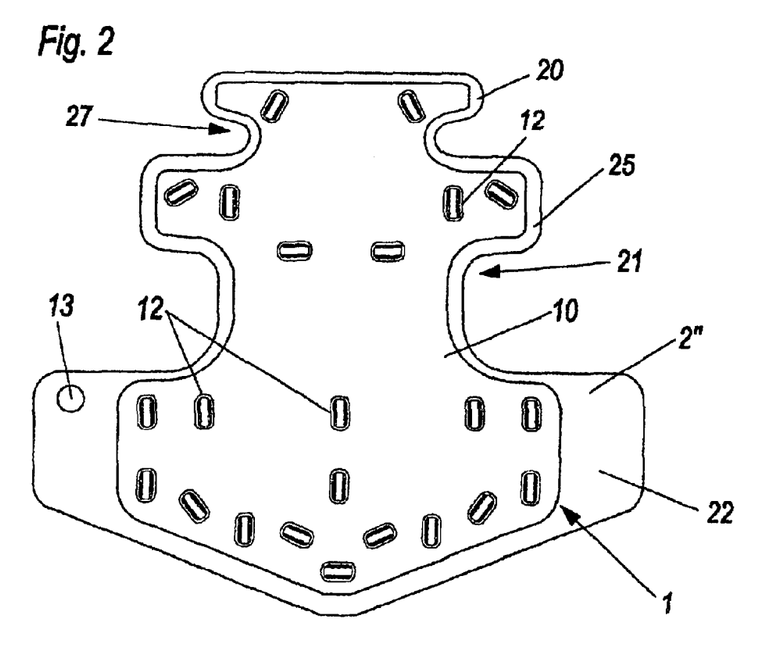
FIG. 2 is a plan view of its outside.

The film element 1 is composed of two airtight films 2', 2" which consist in particular of a polyurethane and are welded to one another along their edges 23. The film 2' which will bear on the injured person is smooth, while an additional stiffening film piece 10 is fixed on the outer film 2" by means of a plurality of mutually intersecting longitudinal and transverse weld seams. The film piece 10 has inlet and outlet slits 12 for fastening straps 11 which extend in part between the film piece 10 and the outer film 2" and are provided at their ends (not shown) with conventional attachment means. Except for lower straps 11', which are used for fixing to the thighs, the straps 11 extend in the circumferential direction of the upper body which is to be enclosed. A valve 13 is arranged in the outer film 2" and is used to evacuate air from the inner space filled with particles 6, for example plastic beads of foamed polystyrene. The film element 1, which is soft and flat prior to use, is intended especially for stabilizing seated injured persons and is placed in the flat state round the injured person's back, drawn forward at the sides, and fixed to the head, trunk and thighs with the aid of the straps. If the air is now evacuated, the film element stiffens in the configuration adapted to the body shape because the particles 6 lose their freedom of movement and they are pressed against one another by the outer air pressure.

Figure 3:
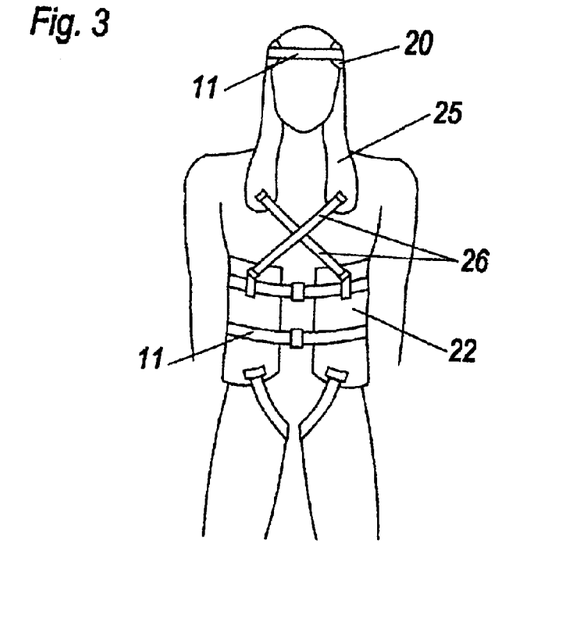
FIG. 3 is a front view of a stabilized patient.
Figure 4:
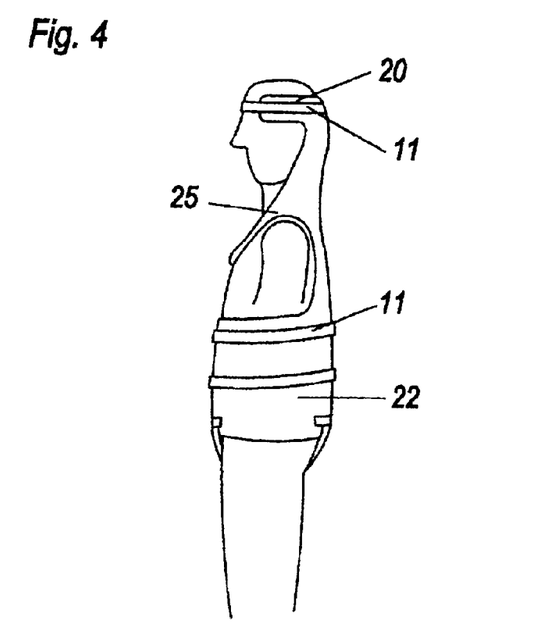
FIG. 4 is a side view of the patient.

In the embodiment according to FIGS. 1–6, the film element 1 has laterally projecting flaps 25 above the arm cutout 21, which flaps 25 can be placed forward round the neck area and down across the shoulders, said flaps ending just below the collarbone area. Obliquely extending and crossed straps 26 connect the flaps 25 to the trunk part 22 (FIGS. 3, 4). Between the flaps 25 and the side ends of the head part 20 there are incisions 27 which, as FIG. 4 shows, leave the middle area of the face free. The head part 20 is reduced to a narrow strip in the area of the temples and forehead of the injured person. In the embodiment according to FIGS. 7 and 8, the head part 22 is higher and extends to the arm cutout 21, so that the side areas lie directly on the shoulder. The design otherwise corresponds to that described with reference to FIGS. 1 and 2.

Figure 5:
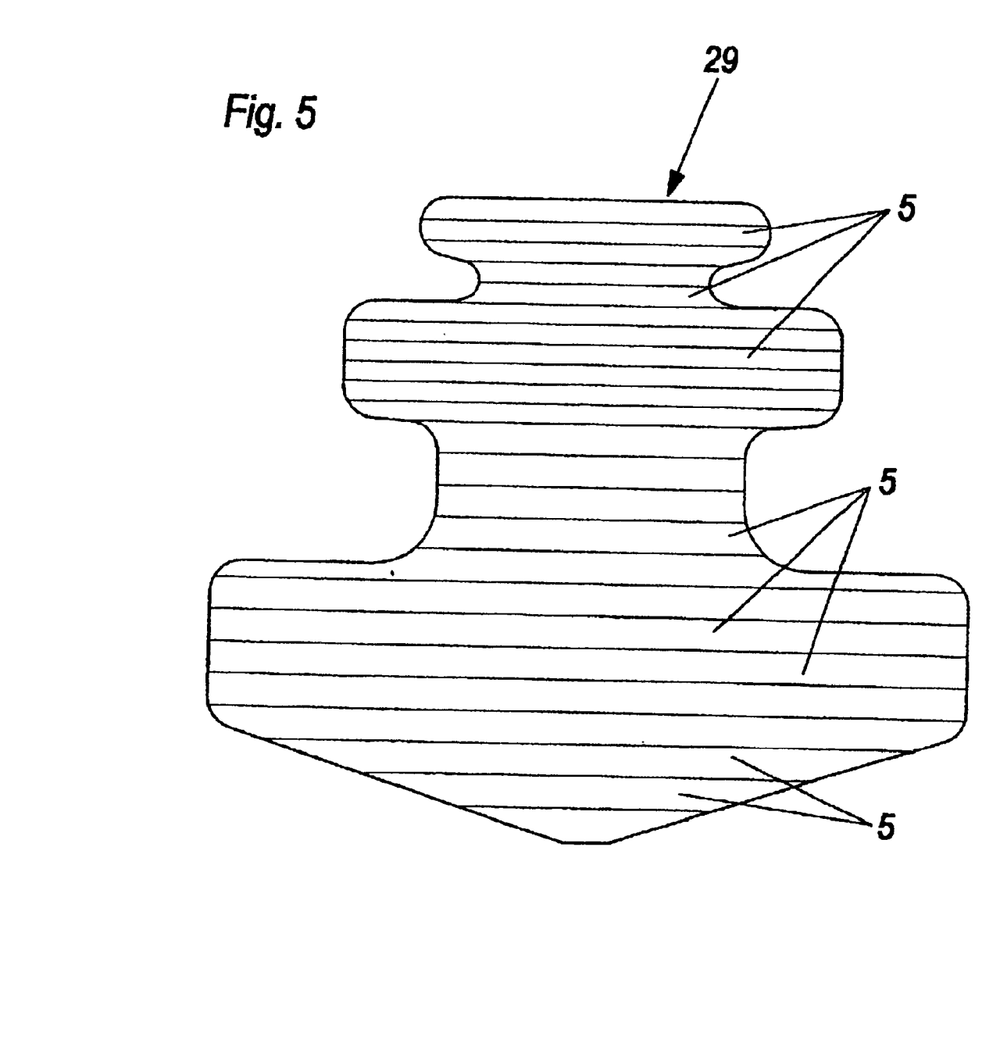
FIG. 5 is a schematic view of the chamber distribution.
Figure 6:
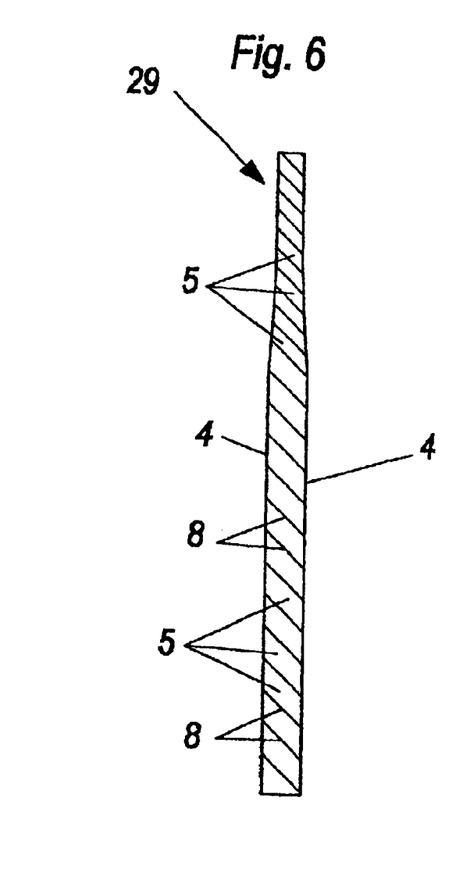
FIG. 6 is a cross section along line VI—VI in FIG. 5.

In order to prevent the particles 6 from slipping downward while the arrangement is placed on the seated person, wherein case too few particles would be present in the upper areas, especially in the head part 20, to achieve the desired stiffening, the inner space of the film element 1 is divided into narrow chambers 5 in each of which the particles 6 are arranged. The longitudinal extent of the narrow chambers 5 is parallel to the straps 11 and therefore in the circumferential direction of the body part that is to be stabilized, and therefore horizontal when used in the upright position, so that the filling is prevented from falling downward. As FIGS. 5 and 6 show, upper chambers 5 of the head part 20 can be narrower than lower chambers 5 of the trunk part 22. To be able to produce such a film element 1 easily and economically, there are various possibilities shown in FIGS. 9 through 12.

Figure 9:
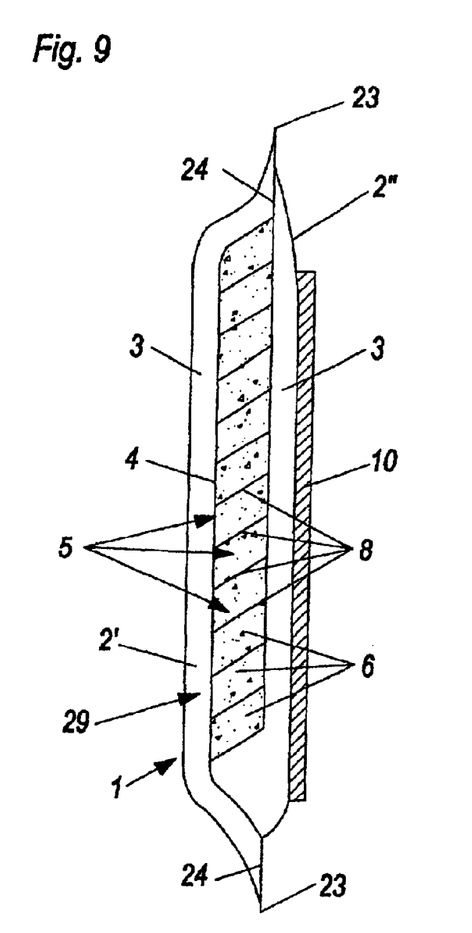
FIGS. 9 through 12 are cross sections along line X—X in FIG. 7 through four different illustrative embodiments.

FIG. 9 shows an embodiment wherein the inner space of the film element 1 is divided into three compartments 3 by two air-permeable dividing walls 4. The two outer compartments 3 are empty and therefore contain only air. The middle compartment is divided by oblique webs 8 into said chambers 5 filled with particles 6. The oblique position of the webs 8 ensures an approximately uniformly thick layer of particles 6 across the entire surface of the film element 1. The two dividing walls 4 and the webs 8 represent an insert body 29 which can be prefabricated and which, after being filled with the particles 6, is connected along its edge 24 to the film 2'. The second film 2" can then be connected to the film 2' provided with the insert body.

Figure 10:
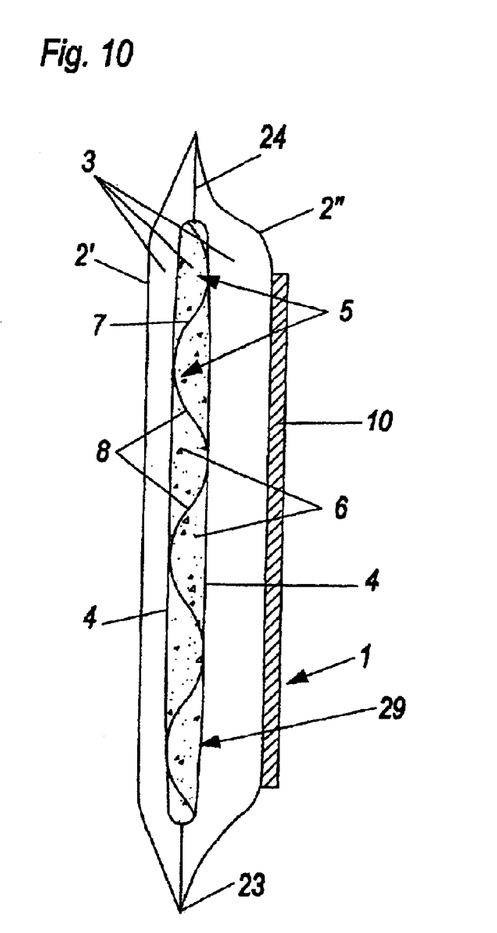

The embodiment according to FIG. 10 is similar. Here too, the particles 6 are provided in the middle compartment 3, the chambers 5 being divided by an undulating insert 7 which forms the oblique webs 8 and is fixed alternately to the two dividing walls 4. Here too, the two dividing walls 4 together with the undulating insert 7 represent a prefabricated insert body 29 which is connected along its edge 24 to the film 2' before the second film 2" is applied.

Figure 11:
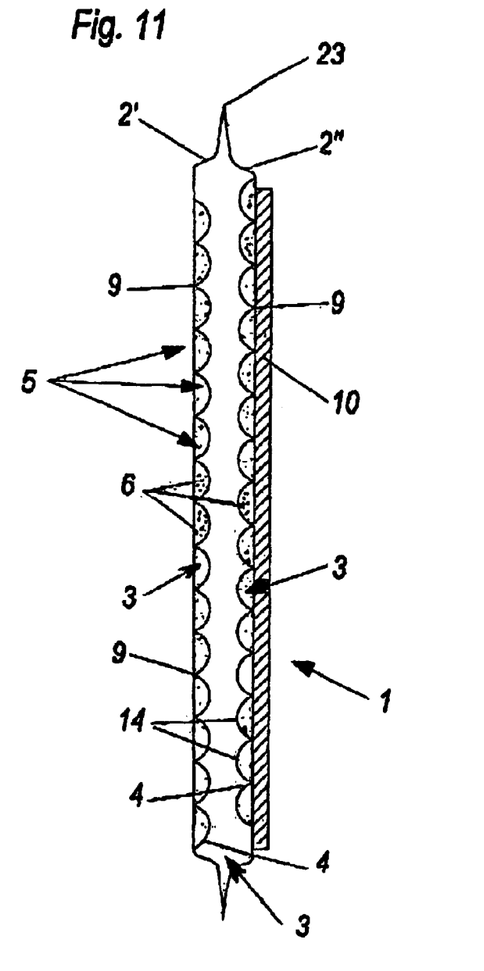

FIG. 11 shows a further embodiment wherein the inner space of the film element 1 is divided into compartments 3 by two dividing walls 4, but the two outer compartments 3 contain particle-filled chambers 5 while the middle compartment 3 is empty. The chambers 5 in this embodiment are formed by connecting seams 9 arranged parallel to one another and 5 between the air-permeable dividing wall 4 and the film 2' or 2". In order to ensure that the layer of particles 6 is approximately uniformly thick across the entire surface of the film element 1, the connecting seams 9 opposite one another are offset in each case by half the width of the chambers 5. When the air is evacuated from the film element 1, an apex 14 of a chamber 5 thus inserts itself into the area of a connecting seam 9 on the opposite side. In this embodiment, the inner sides of the films 2', 2" are each first connected to a dividing wall 4, and the chambers 5 are produced and filled. The two films 2', 2" are then once again welded to one another along their edges 23.

Figure 12:
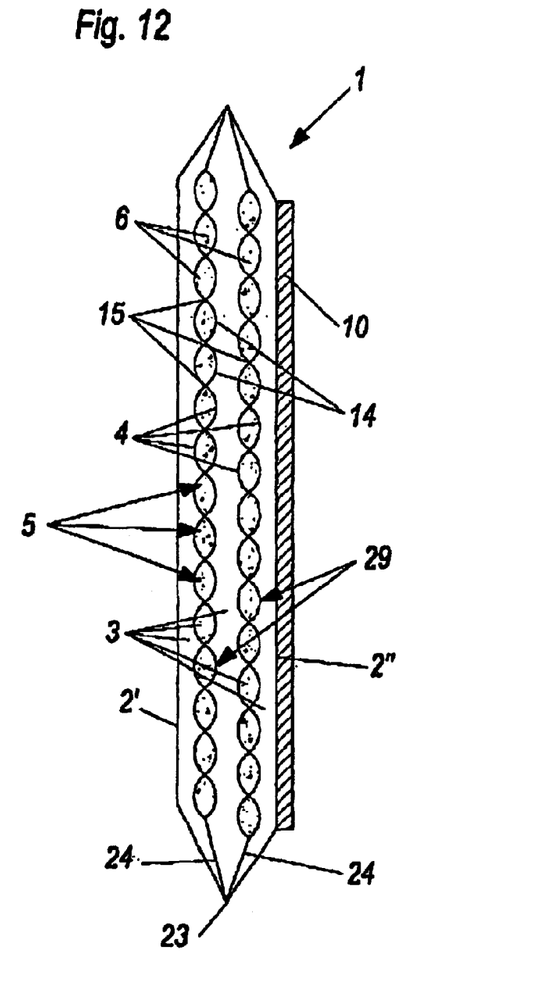

A fourth embodiment is shown in FIG. 12. Here, the inner space is divided into five compartments 3 by four dividing walls 4, with chambers 5 being formed in the second and fourth compartments 3 and the two outermost compartments and the middle compartment remaining empty, i.e. containing only air. Here, the chambers 5 are each connected by directly parallel connecting seams 15 of the two dividing walls 4. There are therefore two insert bodies 29 that can be prefabricated, each of which is secured on the inside of one of the two films 2', 2" along its edge 24. Here too, the connecting seams 15 of the two insert bodies 29 are offset by half the width of the chambers so that, when the inner space is evacuated, each apex 14 fits snugly into the area of the opposite connecting seam 15.

The air-permeable dividing walls 4 and the oblique webs 8 and insert 7 are preferably made of a woven fabric of polypropylene fibers. The connections 15 between the woven fabrics are therefore preferably sewn, and the connections 9 to the films 2', 2" preferably welded.

Figure 7:
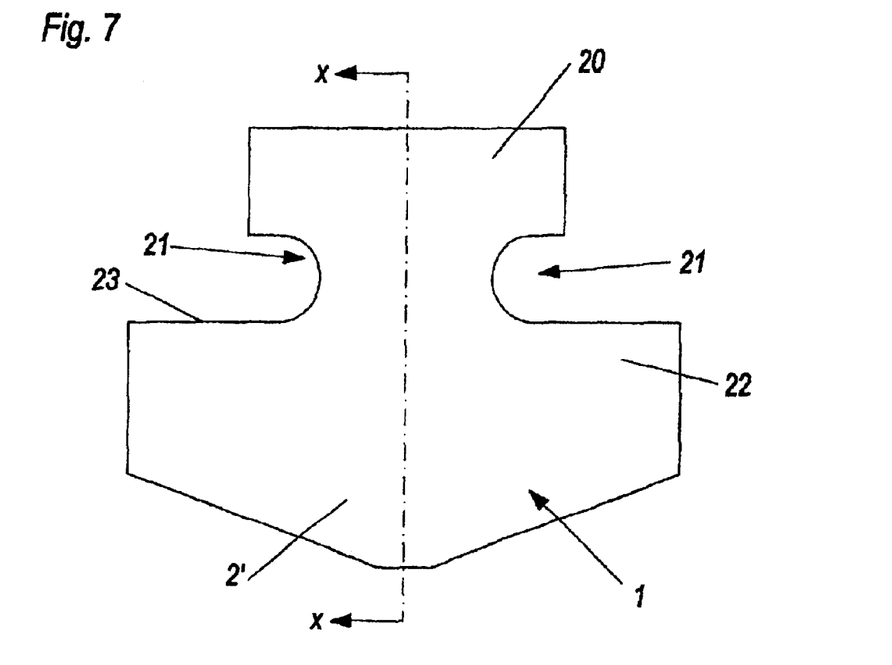
FIG. 7 is a plan view of a second embodiment of an arrangement for stabilizing the upper body and head, showing the side which bears on the patient.
Figure 8:
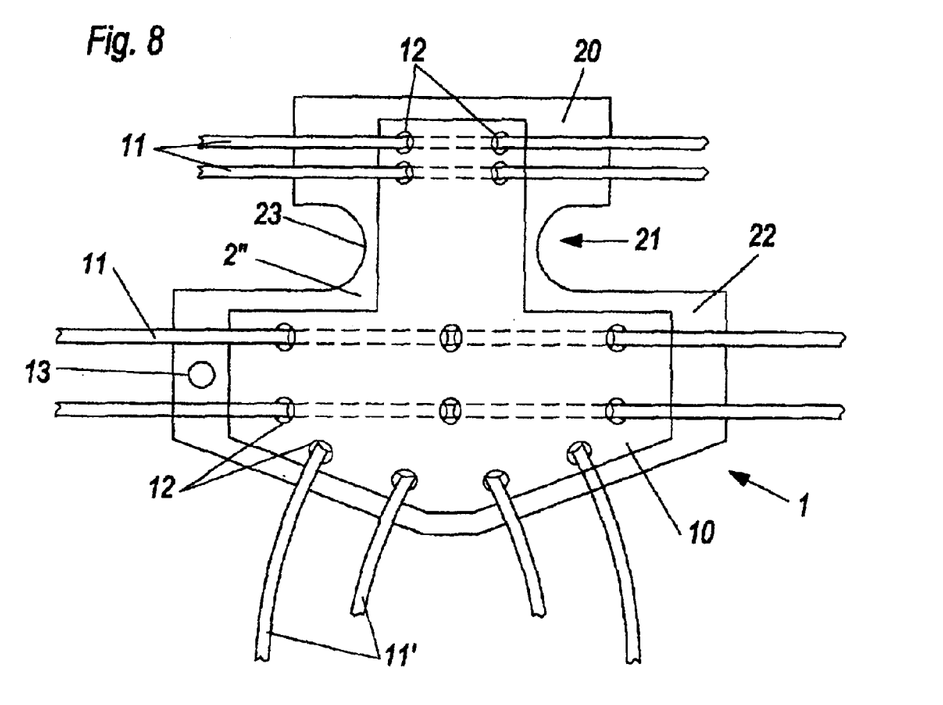
FIG. 8 is a plan view of the outside of the second embodiment.

A further embodiment of a film element can be used for stabilizing and supporting the neck area alone, and it then has approximately the shape shown in FIG. 1 or 7, but with a much shorter trunk part 22. This embodiment therefore represents a neck support sleeve which can be used independently of the body size.

We claim:

1. A configuration for supporting and stabilizing the upper body of an injured person, with a flexible film element which can be placed on the upper body and whose two films enclose an airtight evacuable inner space wherein chambers are provided which contain loose particles, wherein the arrangement has a trunk part, a head part, provided on both sides with a shoulder support, fastening straps which can be closed in the circumferential direction of the respective body part, wherein the chambers extend parallel to the fastening straps, wherein the fastening straps are arranged at least in part between the film, directed away from the injured body part, and an additional film piece.

2. The configuration according to claim 1, wherein each shoulder support is provided with straps for connection to the front of the trunk part.

3. The configuration according to claim 1, wherein the additional film piece is fastened to the film by means of mutually intersecting connecting seams.

4. The configuration according to claim 1, wherein the chambers partially superpose one another in such a way that, with the inner space evacuated, particles from adjacent chambers complement one another to give a substantially uniform particle layer.

5. The configuration according to claim 1, wherein the inner space is divided into at least three compartments by at least two air-permeable flexible dividing walls, and the chambers are formed in at least one of the three compartments.

6. A configuration for supporting and stabilizing an injured body part, with a flexible film element which can be secured round the body part and whose two films enclose an airtight evacuable inner space wherein elongate chambers are provided which contain loose particles, wherein the inner space is divided into at least three compartments by at least two air-permeable flexible dividing walls, and the chambers are formed at least in the middle compartment of the three compartments and are formed by oblique webs between the two flexible dividing walls, and the oblique webs are formed by an undulating insert connected to the two flexible dividing walls at each area of return.

7. The configuration according to claim 6, wherein the inner space is divided into five compartments by four flexible dividing walls, and the chambers are provided in the second and fourth compartments and are formed by a plurality of parallel connecting seams between in each case two flexible dividing walls, the connecting seams opposite one another being offset parallel to one another by in each case half the width of the chamber.

8. The configuration according to claim 6, wherein the chambers are provided in the two outer compartments of three compartments and are formed by a plurality of parallel connecting seams between in each case one film of the film element and the adjacent flexible dividing wall, the connecting seams opposite one another being offset parallel to one another by in each case half the width of the chamber.

9. The configuration according to claim 6, wherein two air-permeable flexible dividing walls are connected to one another along their edges to form an insert body which contains the particles and which is arranged between the edges of the two films and is connected to these.

10. The configuration according to claim 6, wherein the flexible dividing walls are made from lengths of fabric.

11. The configuration according to claim 6, wherein the width of the chambers of the head part is smaller than the width of the chambers of the trunk part.

12. The configuration according to claim 6, wherein it is designed as a neck support sleeve.

13. A configuration for supporting and stabilizing an injured body part, comprising:

a flexible film element which can be secured round the body part and which has two films enclosing an airtight evacuable inner space, air-permeable flexible dividing walls dividing said inner space into compartments, and elongate chambers provided in at least one of said compartments and containing loose particles, wherein said chambers superpose one another in such a way that, with the inner space evacuated, particles from adjacent chambers complement one another to give a substantially uniform particle layer;

wherein the inner space is divided into five compartments by four air-permeable flexible dividing walls and the chambers are provided in the second and fourth compartments and are formed by a plurality of parallel connecting seams between in each case two flexible dividing walls, the connecting seams opposite one another being offset parallel to one another by in each case half the width of the chamber.

14. The configuration according to claim 13, wherein the chambers are provided in the middle compartment of three compartments and are formed by oblique webs between the two flexible dividing walls.

15. The configuration according to claim 14, wherein two air-permeable flexible dividing walls are connected to one another along their edges to form an insert body which contains the particles and which is arranged between the edges of the two films and is connected to these.

16. The configuration according to claim 13, wherein the flexible dividing walls are made from lengths of fabric.

17. The configuration according to claim 13, wherein it is designed as a neck support sleeve.

18. The configuration according to claim 13, wherein said air-permeable flexible dividing walls are disposed to divide said inner space into more than three compartments.

19. A configuration for supporting and stabilizing an injured body part, comprising:

a flexible film element which can be secured round the body part and which has two films enclosing an airtight evacuable inner space, air-permeable flexible dividing walls dividing said inner space into compartments, and elongate chambers provided in at least one of said compartments and containing loose particles, wherein said chambers superpose one another in such a way that, with the inner space evacuated, particles from adjacent chambers complement one another to give a substantially uniform particle layer, wherein the chambers are provided in the middle compartment of three compartments and are formed by oblique webs between the two flexible dividing walls, and wherein the oblique webs are formed by an undulating insert connected to the two flexible dividing walls at each area of return.

20. A configuration for supporting and stabilizing an injured body part, comprising:

a flexible film element which can be secured round the body part and which has two films enclosing an airtight evacuable inner space, air-permeable flexible dividing walls dividing said inner space into compartments, and elongate chambers provided in at least one of said compartments and containing loose particles, wherein said chambers superpose one another in such a way that, with the inner space evacuated, particles from adjacent chambers complement one another to give a substantially uniform particle layer, wherein the chambers are provided in the two outer compartments of three compartments and are formed by a plurality of parallel connecting seams between in each case one film of the film element and the adjacent flexible dividing wall, the connecting seams opposite one another being offset parallel to one another by in each case half the width of the chamber.

21. A configuration for supporting and stabilising the upper body of an injured person, comprising a trunk part and a head part, said head part being provided on both sides with a shoulder support;

a flexible film element which can be secured round the body part and which has two films enclosing an airtight evacuable inner space, air-permeable flexible dividing walls dividing said inner space into compartments, and elongate chambers provided in at least one of said compartments and containing loose particles, wherein said chambers superpose one another in such a way that, with the inner space evacuated, particles from adjacent chambers complement one another to give a substantially uniform particle layer;

wherein the inner space is divided into five compartments by four air-permeable flexible dividing walls and the chambers are provided in the second and fourth compartments and are formed by a plurality of parallel connecting seams between in each case two flexible dividing walls, the connecting seams opposite one another being offset parallel to one another by in each case half the width of the chamber;

and said chambers having a width extending lengthwise of the upper body, the width of the chambers of the head part being smaller than the width of the chambers of the trunk part.

22. The configuration according to claim 21, wherein each shoulder support is provided with straps for connection to the front of the trunk part.

23. The configuration according to claim 21, with fastening straps which can be closed in the circumferential direction of the respective body part, wherein the chambers extend parallel to the fastening straps.

24. The configuration according to claim 23, wherein the fastening straps are arranged at least partially between the film directed away from the injured body part, and an additional film piece.

25. The configuration according to claim 24, wherein the additional film piece is fastened to the film by means of mutually connecting seams.

* * * * *